US012078615B2

United States Patent
Schaller et al.

(10) Patent No.: US 12,078,615 B2
(45) Date of Patent: Sep. 3, 2024

(54) PHOTOACOUSTIC DETECTOR UNIT, PHOTOACOUSTIC SENSOR AND ASSOCIATED PRODUCTION METHODS

(71) Applicant: Infineon Technologies AG, Neubiberg (DE)

(72) Inventors: Rainer Markus Schaller, Saal a.d. Donau (DE); Matthias Eberl, Taufkirchen (DE); Simon Gassner, Munich (DE); Franz Jost, Stuttgart (DE); Stefan Kolb, Unterschleissheim (DE)

(73) Assignee: Infineon Technologies AG, Neubiberg (DE)

(*) Notice: Subject to any disclaimer, the term of this patent is extended or adjusted under 35 U.S.C. 154(b) by 0 days.

(21) Appl. No.: 18/322,755

(22) Filed: May 24, 2023

(65) Prior Publication Data

US 2023/0296567 A1    Sep. 21, 2023

Related U.S. Application Data

(62) Division of application No. 17/247,134, filed on Dec. 1, 2020, now Pat. No. 11,733,213.

(30) Foreign Application Priority Data

Dec. 13, 2019 (DE) .......................... 102019134267.8

(51) Int. Cl.
*G01N 29/24*    (2006.01)
*G01N 33/00*    (2006.01)

(52) U.S. Cl.
CPC ..... *G01N 29/2425* (2013.01); *G01N 33/0004* (2013.01)

(58) Field of Classification Search
CPC .. G01N 29/2425; G01N 29/30; G01N 29/343; G01N 29/348; G01N 33/0004; G01N 2021/1704; G01N 21/1702; G01N 2291/021
See application file for complete search history.

(56) References Cited

U.S. PATENT DOCUMENTS

| | | | |
|---|---|---|---|
| 4,682,897 A | 7/1987 | Saito et al. | |
| 9,513,261 B2 | 12/2016 | Dehe et al. | |
| 10,451,543 B2 | 10/2019 | Mueller et al. | |
| 10,458,900 B2 | 10/2019 | Marta et al. | |
| 10,495,612 B2* | 12/2019 | Dehe | G01N 21/1702 |
| 11,530,980 B2 | 12/2022 | Kolb et al. | |
| 2016/0313288 A1 | 10/2016 | Theuss et al. | |

(Continued)

FOREIGN PATENT DOCUMENTS

| | | |
|---|---|---|
| CN | 104568757 A | 4/2015 |
| CN | 106153548 A | 11/2016 |

(Continued)

*Primary Examiner* — Suman K Nath
(74) *Attorney, Agent, or Firm* — Harrity & Harrity, LLP (57) ABSTRACT

A photoacoustic detector unit comprises a housing having an opening, and also a photoacoustic transducer designed to convert optical radiation into at least one from a pressure signal or a heat signal. The photoacoustic transducer covers the opening of the housing, such that the photoacoustic transducer and the housing form an acoustically tight cavity. A pressure pick-up is arranged in the acoustically tight cavity.

20 Claims, 7 Drawing Sheets

(56) References Cited

U.S. PATENT DOCUMENTS

| | | |
|---|---|---|
| 2017/0067859 A1 | 3/2017 | Kolb et al. |
| 2017/0290097 A1 | 10/2017 | Pindl et al. |
| 2018/0273373 A1 | 9/2018 | Pindl |
| 2019/0161343 A1 | 5/2019 | Koley et al. |
| 2019/0352175 A1 | 11/2019 | Tumpold et al. |
| 2020/0080972 A1 | 3/2020 | Dehe et al. |
| 2020/0249149 A1* | 8/2020 | Theuss ............... G01N 21/1702 |
| 2021/0181158 A1 | 6/2021 | Schaller et al. |

FOREIGN PATENT DOCUMENTS

| | | |
|---|---|---|
| CN | 108351294 A | 7/2018 |
| CN | 109313129 A | 2/2019 |
| DE | 102014114672 A1 | 4/2015 |
| DE | 102016103646 A1 | 7/2017 |
| DE | 102018207605 A1 | 11/2019 |
| JP | S56154634 A | 11/1981 |
| WO | 2017207399 A1 | 12/2017 |

* cited by examiner

PHOTOACOUSTIC DETECTOR UNIT, PHOTOACOUSTIC SENSOR AND ASSOCIATED PRODUCTION METHODS

CROSS REFERENCE TO RELATED APPLICATIONS

This application is a divisional of U.S. patent application Ser. No. 17/247,134, filed Dec. 1, 2020, which claims priority to Germany Patent Application No. 102019134267.8, filed on Dec. 13, 2019, the contents of which are incorporated by reference herein in their entireties.

TECHNICAL FIELD

The present disclosure relates to photoacoustic detector units, photoacoustic sensors and associated production methods.

BACKGROUND

Photoacoustic sensors can detect specific gas species in the ambient air, for example. In particular, harmful or hazardous components in the ambient air can be detected in this case. The correct functioning of such sensors can thus be of extremely high importance in many applications, particularly if the sensors are used for the safety of work personnel. Photoacoustic sensors can be constructed from a plurality of components and generally consist of an emitter unit and a detector unit.

BRIEF SUMMARY

Implementations described herein may provide photoacoustic detector units configured to effectively detect different gas species in the ambient air. Furthermore, implementations described herein may provide cost-effective methods for producing such photoacoustic detector units. A first aspect relates to a photoacoustic detector unit. The photoacoustic detector unit comprises a housing having an opening. The photoacoustic detector unit furthermore comprises a photoacoustic transducer designed to convert optical radiation into at least one from a pressure signal or a heat signal, wherein the photoacoustic transducer covers the opening of the housing, such that the photoacoustic transducer and the housing form an acoustically tight cavity. The photoacoustic detector unit furthermore comprises a pressure pick-up arranged in the acoustically tight cavity.

A second aspect relates to a photoacoustic sensor. The photoacoustic sensor comprises an optical emitter and a photoacoustic detector unit in accordance with the first aspect.

A third aspect relates to a method. The method comprises bonding a first wafer composed of a first material to a second wafer composed of a second material in a reference gas atmosphere, wherein a plurality of hermetically sealed cavities are formed, which enclose the reference gas of the reference gas atmosphere. The method furthermore comprises singulating the bonded wafers into a plurality of photoacoustic transducers for a photoacoustic detector unit, wherein each of the photoacoustic transducers comprises one of the hermetically sealed cavities.

BRIEF DESCRIPTION OF THE DRAWINGS

Photoacoustic detector units, photoacoustic sensors and associated production methods in accordance with the disclosure are explained in greater detail below with reference to drawings. The elements shown in the drawings are not necessarily rendered in a manner true to scale relative to one another. Identical reference signs may designate identical components.

DETAILED DESCRIPTION

The figures described below show photoacoustic detector units, photoacoustic sensors and associated production methods in accordance with the disclosure. In this case, the described devices and methods may be illustrated in a general way in order to describe aspects of the disclosure qualitatively. The devices and methods described may have further aspects that may not be illustrated in the respective figure for the sake of simplicity. However, the respective example can be extended by aspects described in association with other examples in accordance with the disclosure. Consequently, explanations concerning a specific figure may equally apply to examples of other figures.

Figure 1:
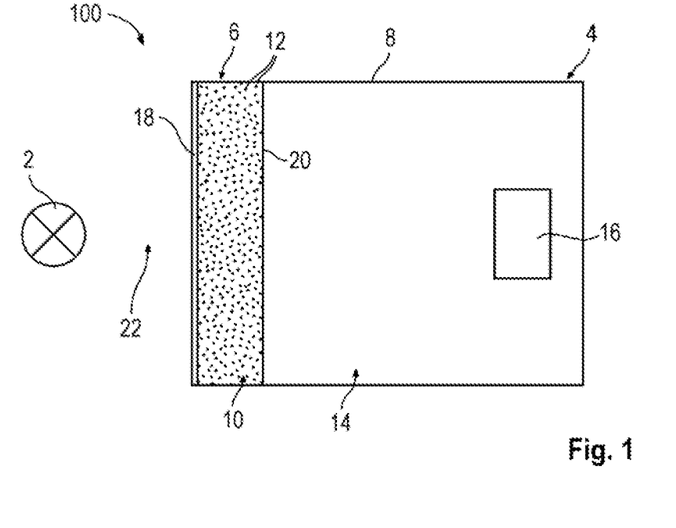
FIG. 1 shows a schematic view of a photoacoustic sensor 100 in accordance with the disclosure.

The photoacoustic sensor or photoacoustic gas sensor 100 in FIG. 1 can comprise a photoacoustic emitter unit 2 and a photoacoustic detector unit 4. The photoacoustic detector unit 4 can comprise a photoacoustic transducer 6 and a housing 8. The photoacoustic transducer 6 can be a cell having a hermetically sealed cavity 10, in which a reference gas 12 can be enclosed. The photoacoustic transducer 6 can have an optically transparent window 18 on a first side and a membrane 20 on a second side situated opposite the first side. The photoacoustic transducer 6 can cover an opening of the housing 8, such that the photoacoustic transducer 6 and the housing 8 can form an acoustically tight cavity 14. A pressure pick-up 16 can be arranged in the acoustically tight cavity 14.

Furthermore, a protective gas can optionally be enclosed in the acoustically tight cavity 14. The protective gases specified in this description can be, for example, nitrogen or a noble gas, such as e.g. argon, xenon, krypton. Furthermore, depending on the application, one or more alternative or additional components can be arranged in the acoustically tight cavity 14, for example one or more from a pressure pick-up ASIC, a photodetector, a photodiode, a temperature sensor, an optical emitter.

The photoacoustic emitter unit 2 can be a broadband emitter, which can be designed to emit optical radiation over a wide frequency range. In other words, the radiation emitted by the broadband emitter can comprise not just predetermined frequencies or predetermined frequency bands. The term "optical radiation" used in this description can generally refer to a partial range of the electromagnetic spectrum having wavelengths of between approximately 100 nm and approximately 100 μm. That is to say that the optical radiation can comprise, in particular, at least one from the following: ultraviolet radiation having a wavelength of approximately 100 nm to approximately 380 nm, infrared radiation having a wavelength of approximately 780 nm to approximately 100 μm, or radiation having a wavelength of approximately 780 nm to approximately 5 μm, e.g. near-infrared radiation and portions of mid-infrared radiation. The last-mentioned range can comprise, inter alia, the absorption lines/bands of carbon dioxide at 4.26 μm and of further gas species. Even more specifically, the optical radiation can have a wavelength of approximately 300 nm to approximately 20 μm.

The photoacoustic emitter unit 2 can be designed to emit optical pulses having a predetermined repetition frequency and one or more predetermined wavelengths. In this case, a predetermined wavelength can comprise an absorption band of a gas to be detected or of the reference gas 12. The repetition frequency of the optical pulses can be within a low-frequency range or within a frequency range of approximately 1 Hz to approximately 10 kHz, in particular of approximately 1 Hz to approximately 1 kHz. Even more specifically, a typical frequency range can be between approximately 1 Hz and approximately 100 Hz, corresponding to a pulse duration range of approximately 0.01 s to approximately 1 s.

A manner of functioning of the photoacoustic sensor 100 is described below. The optical pulses emitted by the emitter unit 2 can pass through an interspace 22 situated between the emitter unit 2 and the detector unit 4. By way of example, the interspace 22 can be filled with ambient air. During propagation through the interspace 22, the optical pulses can be at least partly absorbed by portions of a gas to be detected if such a gas is present in the interspace 22 (e.g. in the ambient air). The absorption can be specific to the gas to be detected, e.g. characteristic rotation or vibration modes of atoms or molecules of the gas to be detected.

The optical pulses can pass through the material of the optically transparent window 18 and impinge on atoms or molecules of the reference gas 12 in the hermetically sealed cavity 10. The reference gas 12 can correspond to the gas to be detected. The reference gases mentioned in this description can be, for example, carbon dioxide, nitrogen oxide, methane, ammonia. The optical pulses can at least partly be absorbed by the reference gas 12 and bring about local pressure increases in the reference gas 12. The pressure increases can be passed on to the membrane 20 and through the latter into the acoustically tight cavity 14. In other words, the photoacoustic transducer 6 can be designed to convert optical radiation in the form of e.g. optical pulses into pressure signals. The photoacoustic transducer 6 is acoustically coupled to the acoustically tight cavity 14.

As an alternative or in addition to the pressure signals described, the photoacoustic transducer 6 can convert the optical radiation into heat signals. In this context, the photoacoustic transducer 6 can also be referred to as a photothermal transducer. In this case, the membrane 20 can be heated by absorption of the optical pulses, in particular with the predetermined repetition frequency of the optical pulses. As a result of the periodic heating and cooling of the membrane 20, pressure changes can be produced in the downstream acoustically tight cavity 14, which pressure changes can be detected by the pressure pick-up 16.

Generally, the photoacoustic transducers in accordance with the disclosure as described herein can accordingly convert optical radiation into at least one from a pressure signal or a heat signal. In this case, the type of signal generated can be dependent on the respective configuration of the photoacoustic transducer. A conversion into a pressure signal can be provided in particular by way of a deflection or mechanical bending of the membrane, while a conversion into a heat signal can be provided in particular by heating and cooling of the membrane. Depending on the configuration of the respective photoacoustic transducer, a conversion into a pressure signal and/or a heat signal can take place. Pressure signals and heat signals generated can both be detected by a downstream acoustically tight cavity with pressure pick-up. Furthermore, the pressure signals can also be detected in the membrane itself, for example by one or more piezo-elements integrated into the membrane.

The expression "acoustically tight" used for the cavity 14, for example, need not necessarily mean in this description that the cavity 14 is hermetically or completely sealed. Rather, the walls forming the cavity 14 can be designed to provide, during operation of the photoacoustic sensor 100, pressure equalization with the surroundings such that the pressure pick-up 16 can be operated properly. In this case, it cannot be excluded, for example, that the walls of the cavity 14 have one or more small openings which do not influence, or which influence only negligibly, the pressure equalization for proper operation. The term "acoustically tight" can optionally be replaced by the term "semi-hermetic".

The pressure signals and/or heat signals passed on by the membrane 20 can be detected by the pressure pick-up 16 in the acoustically tight cavity 14. The pressure pick-ups specified in this description can be, for example, microphones or any other type of pressure sensors or pressure-sensitive sensors. The signals detected by the pressure pick-up 16 can be processed logically by one or more circuits. By way of example, such signal processing can be carried out by an ASIC.

If no portions of a gas to be detected are present in the interspace 22 or in the ambient air, the optical pulses emitted by the emitter unit 2 are merely absorbed by the reference gas 12 and the pressure pick-up 16 will detect a periodic measurement signal with the repetition frequency of the optical pulses and a first amplitude. If, in contrast thereto, portions of a gas to be detected are present in the interspace 22, the optical radiation can additionally be absorbed by the portions. The pressure pick-up 16 will then output a periodic measurement signal having a second amplitude, which can be smaller than the first amplitude. A presence and/or a concentration of the gas to be detected in the ambient air can be determined on the basis of the magnitudes and profiles of the first and second amplitudes. If the concentration of the gas to be detected exceeds a predetermined threshold value, for example a signal, in particular a warning signal, can be output by the photoacoustic sensor 100 or a device connected thereto.

Using a broadband emitter 2 and a photoacoustic transducer 6 containing the species of a gas to be detected in its cavity 10, any gas species whose absorption bands lie in the spectrum of a black body radiator can be detected by the photo acoustic sensor 100 in FIG. 1.

In conventional photoacoustic sensors, the pressure pick-up and the reference gas can be arranged in a common hermetically sealed cavity. Sealing the cavity and simultaneously filling the cavity with the reference gas can be demanding in terms of process engineering. In contrast thereto, the reference gas 12 in accordance with the present disclosure can be arranged in the cell of the photoacoustic transducer 6. As a result, during the production of the photoacoustic sensor 100, the process steps mentioned can be decoupled from mounting the pressure pick-up 16 in the cavity 14.

In the case of the conventional photoacoustic sensors, the photoacoustic conversion can be provided in particular in the common cavity in which the reference gas and the pressure pick-up are arranged. In contrast thereto, in the case of the photoacoustic sensor 100 in accordance with the disclosure, the photoacoustic conversion can be provided in a separate hermetically sealed cavity 10 disposed upstream of the acoustically tight cavity 14 with the pressure pick-up 16 arranged therein. In accordance with the disclosure, the cavities 10 and 14 with reference gas 12 and pressure pick-up 16, respectively, can be decoupled from one another.

In the case of the described construction of the photoacoustic sensor 100, the pressure pick-up 16 can have an extremely high sensitivity, as a result of which an extremely high sensitivity of the photoacoustic sensor 100 can be provided. As a result, it is possible to achieve a reduced energy consumption during operation of the photoacoustic sensor 100.

It is evident from the method in FIGS. 12A-E described further below that the photoacoustic sensor 100 or the photoacoustic transducer 6 can be produced on the basis of cost-effective method steps at the wafer level.

Figure 2:
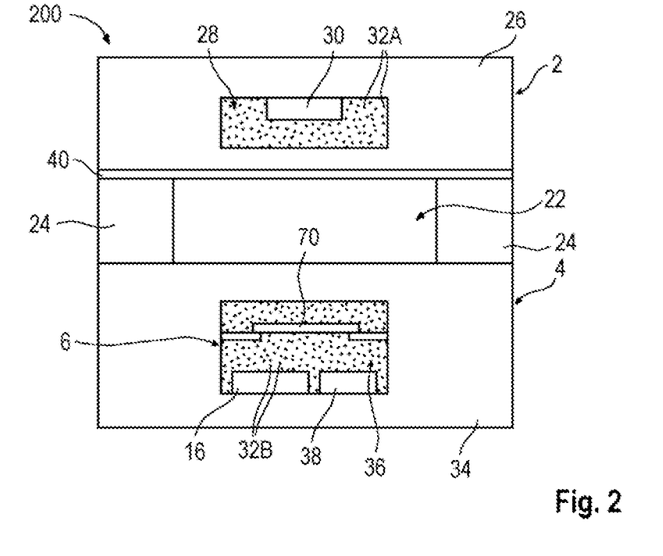
FIG. 2 shows a schematic view of a photoacoustic sensor 200 in accordance with the disclosure.

The photoacoustic sensor or photoacoustic gas sensor 200 in FIG. 2 can comprise a photoacoustic emitter unit 2 and a photoacoustic detector unit 4. The units 2 and 4 can be spaced apart from one another by one or more spacers 24, as a result of which an interspace 22 arranged between the units 2 and 4 can be formed. An optical filter 40 can be arranged between the photoacoustic emitter unit 2 and the photoacoustic detector unit 4. The photoacoustic emitter unit 2 can comprise a housing 26 having an cavity 28, in which an emitter 30 and a protective gas 32A can be arranged. The photoacoustic detector unit 4 can comprise a housing 34 having an cavity 36. A photoacoustic transducer 6 in the form of a membrane 70, a pressure pick-up 16 and a pressure pick-up ASIC 38 can be arranged in the acoustically tight cavity 36. The components of the photoacoustic sensor 200 can be similar to corresponding components of the photoacoustic sensor 100 in FIG. 1, such that explanations concerning FIG. 1 can also apply to FIG. 2.

A manner of functioning of the photoacoustic sensor 200 is described below. The emitter 30 can emit optical radiation, in particular in the form of optical pulses. In this case, the emitter 30 can be for example a broadband emitter that emits optical radiation over a wide frequency range. The (broadband) radiation emitted by the emitter 30 can firstly pass through the protective gas 32A and the housing 26. In this case, the housing 26 can be fabricated from a material that is transparent to the optical radiation, for example from IR-transparent silicon. The emitted radiation can be filtered by the optical filter 40 and pass through the interspace 22. In this case, the optical filter 40 can be or comprise an optical bandpass filter, in particular. The optical bandpass filter 40 can be transmissive to optical radiation having a wavelength which can comprise an absorption band of a gas to be detected. Upon passing through the interspace 22 or the ambient air, the filtered optical radiation can impinge on portions of a gas to be detected if the ambient air contains such portions.

The optical radiation can pass through the upper part of the housing 34 and enter the cavity 36. In this case, at least the upper part of the housing 34 can be fabricated from a material that is transparent to the optical radiation, for example from IR-transparent silicon. In the cavity 36, the optical radiation can impinge on the membrane 70, which can have a low thermal mass, in particular. The membrane 70 can absorb the optical radiation and thereby produce pressure changes in the cavity 36 lying below the membrane 70. The pressure changes can be detected by the pressure pick-up 16. The signals detected by the pressure pick-up 16 can be processed logically by the pressure pick-up ASIC 38.

As already described in association with FIG. 1, the signals detected by the pressure pick-up 16 can depend on whether or not portions of the gas to be detected are present in the interspace 22 or the ambient air. A presence and/or a concentration of the gas to be detected in the ambient air can be determined on the basis of the signals detected.

The photoacoustic sensor 200 can be operated without the use of a reference gas. With the use of a broadband emitter 30 and a suitable optical filter 40, it is possible to detect any gas species in the spectrum of a black body radiator using the photoacoustic sensor 200. In this case, the gas selectivity need not necessarily be provided by the choice of a reference gas, but rather can be provided by the optical filter property of the photoacoustic emitter unit 2 and/or of the optical filter 40.

In the case of the described construction of the photoacoustic sensor 200, the pressure pick-up 16 can have an extremely high sensitivity, as a result of which an extremely high sensitivity of the photoacoustic sensor 200 can be provided. As a result, it is possible to achieve a reduced energy consumption during operation of the photoacoustic sensor 200.

The photoacoustic sensor 200 can be produced on the basis of cost-effective method steps at the wafer level.

Figure 3:
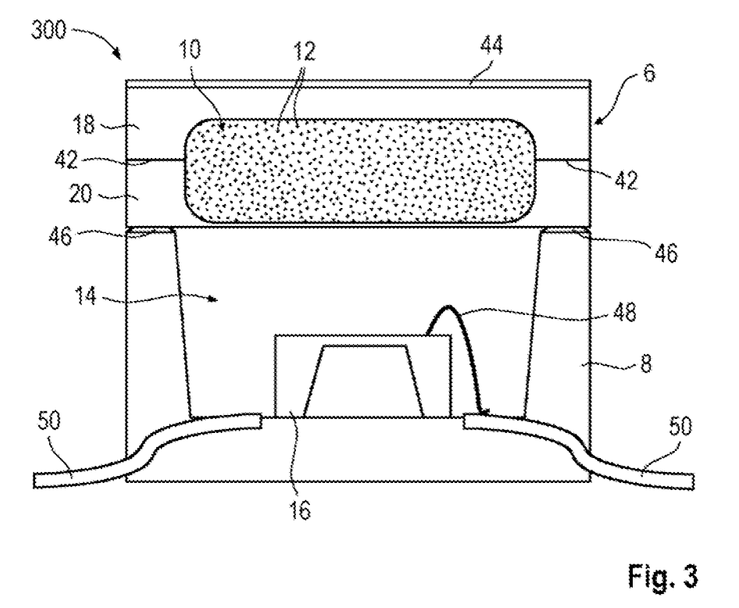
FIG. 3 schematically illustrates a cross-sectional side view of a photoacoustic detector unit 300 in accordance with the disclosure.

The photoacoustic detector unit 300 in FIG. 3 can for example be used in the photoacoustic sensor 100 in FIG. 1 and comprise similar components. With regard to operation of the photoacoustic detector unit 300, reference is made to corresponding explanations concerning FIG. 1.

The photoacoustic detector unit 300 can comprise a photoacoustic transducer 6, which can comprise an optically transparent window 18 and a membrane 20. The optically transparent window 18 and the membrane 20 can form a hermetically sealed cavity 10, which can enclose a reference gas 12. In one example, the optically transparent window 18 can be fabricated from IR-transparent silicon. The membrane 20 can be fabricated from a glass material, for example from a borosilicate. The membrane 20 can be designed to absorb optical radiation such as e.g. IR radiation. As a result of the absorption, the membrane 20 can be heated and generate a heat signal. In other words, the optical radiation can be converted into a heat signal by the membrane 20. On account of the periodic heating and cooling of the membrane 20, pressure changes can be produced in an acoustically tight cavity 14 arranged below the membrane 20. The pressure changes can be detected by a pressure pick-up 16.

The optically transparent window 18 and the membrane 20 can be secured to one another by way of an anodic bond connection 42. It is evident from the method in FIGS. 12A-E as described further below that anodic bonding of the optically transparent window 18 and the membrane 20 can be carried out at the wafer level. An antireflection coating 44 can be arranged on the top side of the window 18, and can be designed to suppress reflection of optical radiation that can be provided by a photoacoustic emitter unit (not illustrated). The transmission of the optically transparent window 18 can be increased by the antireflection coating 44.

The photoacoustic detector unit 300 can furthermore comprise a housing 8, which can form the shape of a shell or a trough. In one example, the housing 8 can be fabricated from a mold compound. The mold compound can include at least one from an epoxy, a filled epoxy, a glass-fiber-filled epoxy, an imide, a thermoplastic, a thermosetting polymer, a polymer mixture. The photoacoustic transducer 6 can cover an opening on the top side of the housing 8, wherein the housing 8 and the photoacoustic transducer 6 can form the acoustically tight cavity 14. In FIG. 3, the photoacoustic transducer 6 and the housing 8 can be connected to one another by an adhesive 46, for example. A protective gas can optionally be enclosed in the acoustically tight cavity 14.

The pressure pick-up 16 can be arranged on the bottom surface of the housing 8. The pressure pick-up can be a microphone chip, for example, which can comprise one or more MEMS structures and/or movable structures. Furthermore, the microphone chip of pressure pick-up 16 can include an ASIC for logically processing the signals detected by the MEMS structures. The microphone chip of pressure pick-up 16 can be electrically connected to one or more connecting conductors 50 by way of one or more electrical connection elements 48. In the example in FIG. 3, the electrical connection element 48 is illustrated as a bond wire, for example. The connecting conductors 50 can extend through the housing 8 and provide an electrical connection between the microphone chip of pressure pick-up 16 and further components (not illustrated) arranged outside the housing 8.

Figure 4:
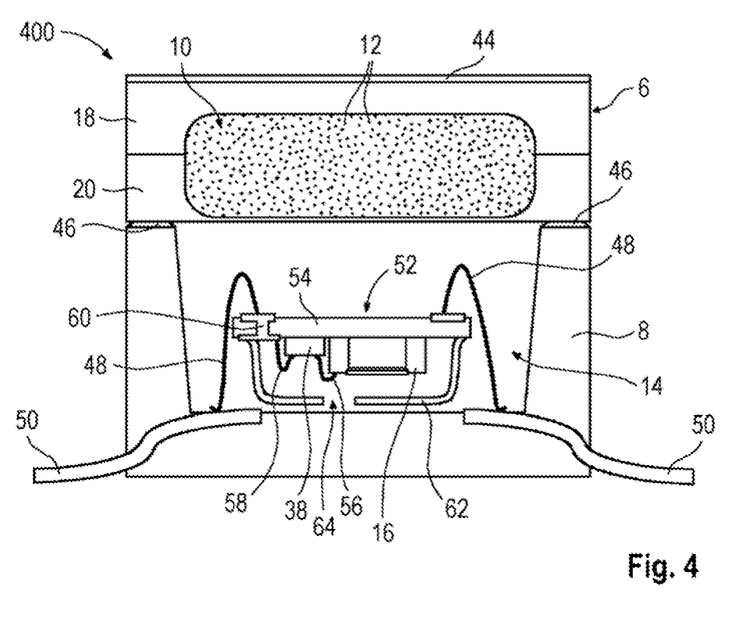
FIG. 4 schematically illustrates a cross-sectional side view of a photoacoustic detector unit 400 in accordance with the disclosure.

The photoacoustic detector unit 400 in FIG. 4 can be used for example in the photoacoustic sensor 100 in FIG. 1. Furthermore, the photoacoustic detector unit 400 can at least partly be similar to the photoacoustic detector unit 300 in FIG. 3 and comprise identical components.

In contrast to FIG. 3, the pressure pick-up 16 in FIG. 4 can be embodied or arranged in a different way. In this case, the pressure pick-up 16 or its MEMS structures can be arranged in particular such that they lie outside a course of the optical radiation provided by a photoacoustic emitter unit (not illustrated). Signals detected by the pressure pick-up 16 can be corrupted by optical radiation impinging on the MEMS structures of the pressure pick-up 16. On account of the arrangement of the pressure pick-up 16 outside the optical path as shown in FIG. 4, such corruption can be avoided or at least reduced.

The photoacoustic detector unit 400 can comprise a pressure pick-up device 52. The pressure pick-up device 52 can comprise a circuit board or a substrate 54 with a pressure pick-up 16 and pressure pick-up ASIC 38 arranged on the underside of the circuit board or the substrate 54. The pressure pick-up 16 and the pressure pick-up ASIC 38 can be electrically connected to one another by way of one or more bond wires 56, for example. Furthermore, the pressure pick-up 16 and the pressure pick-up ASIC 38 can be electrically coupled to the connecting conductors 50 by way of one or more bond wires 58, by way of a wiring layer 60 within the circuit board or the substrate 54 and by way of the electrical connecting elements 48. The pressure pick-up device 52 can comprise a cover 62 having an opening 64, the cover being arranged over the pressure pick-up 16 and over the pressure pick-up ASIC 38.

Figure 5:
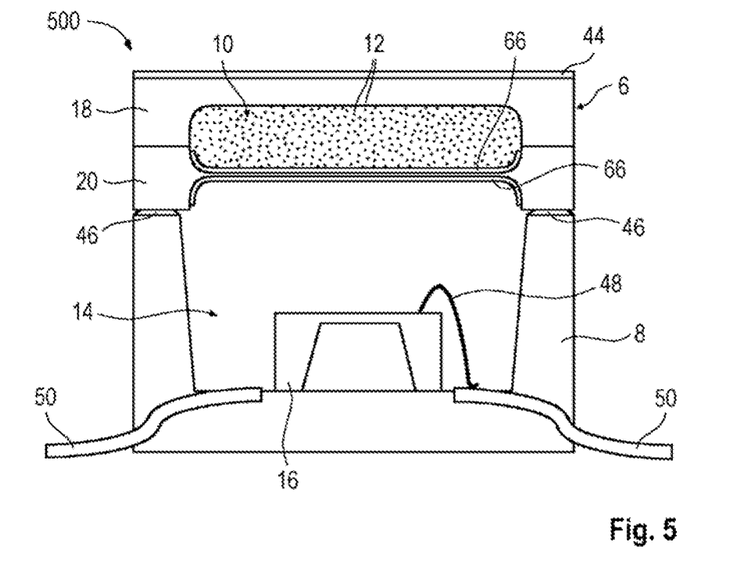
FIG. 5 schematically illustrates a cross-sectional side view of a photoacoustic detector unit 500 in accordance with the disclosure.

The photoacoustic detector unit 500 in FIG. 5 can be used for example in the photoacoustic sensor 100 in FIG. 1. Furthermore, the photoacoustic detector unit 500 can at least partly be similar to the photoacoustic detector unit 300 in FIG. 3 and comprise identical components.

In contrast to FIG. 3, the photoacoustic detector unit 500 can comprise one or more metal layers and/or metal alloy layers 66, which can be arranged on the membrane 20. In the example in FIG. 5, a metal layer 66 can be arranged in each case on the top side and on the underside of the membrane 20. In further examples, a metal layer can be arranged only on the top side or only on the underside of the membrane 20. In the example in FIG. 5, only one metal layer 66 in each case is arranged on the top side and underside. In further examples, a layer stack having a plurality of metal layers stacked one above another can be arranged on the respective side of the membrane 20. In the example in FIG. 5, the respective metal layer 66 can cover substantially the entire exposed surface of the membrane 20. In further examples, the respective metal layer 66 can cover only selected parts of the membrane surfaces. A metal layer 66 arranged on the membrane 20 can have a lower heat capacity in comparison with the membrane 20.

Figure 6:
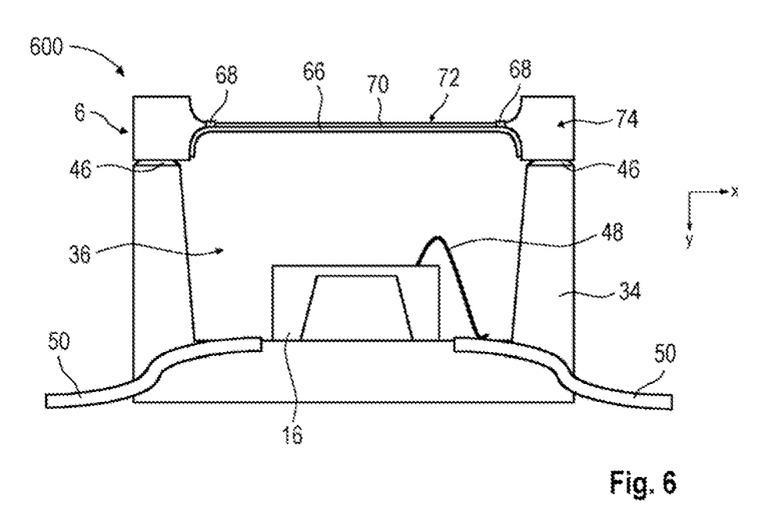
FIG. 6 schematically illustrates a cross-sectional side view of a photoacoustic detector unit 600 in accordance with the disclosure.

The photoacoustic detector unit 600 in FIG. 6 can for example be used in the photoacoustic sensor 200 in FIG. 2 and comprise similar components. With regard to operation of the photoacoustic detector unit 200, reference is made to corresponding explanations concerning FIG. 2.

The photoacoustic detector unit 600 can comprise a housing 34 with a pressure pick-up 16 arranged therein. A photoacoustic transducer 6 in the form of a membrane 70 can cover an upper opening of the housing 34 and form with the latter an acoustically tight cavity 36. The membrane 70 can have an elastic inner region 72 and a thicker edge region 74. The edge region 74 can have the shape of a frame. The inner region 72 can be suspended from or secured to the edge region 74 and be designed to oscillate in the y-direction. As viewed in the y-direction, the inner region 72 can have a circular shape, for example. In the example in FIG. 6, the membrane 70 can be fabricated from a glass material, for example from a borosilicate. The inner region 72 of the membrane 70 can have at its outer regions one or more ventilation holes 68, which can result from a structured suspension of the inner region 72 from the edge region 74 of the membrane 70. In the example in FIG. 6, a metal layer 66 can be arranged on the underside of the membrane 70. In a further example, a further metal layer can be arranged on the top side of the membrane 70.

Figure 7:
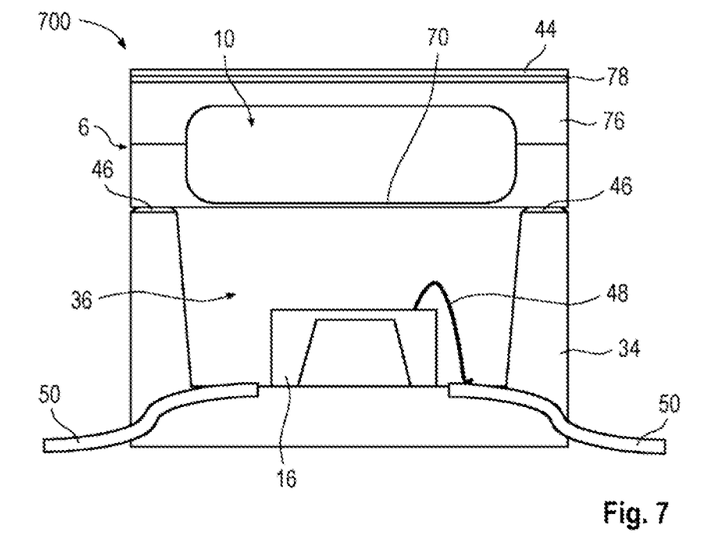
FIG. 7 schematically illustrates a cross-sectional side view of a photoacoustic detector unit 700 in accordance with the disclosure.

The photoacoustic detector unit 700 in FIG. 7 can be used for example in the photoacoustic sensor 200 in FIG. 2. Furthermore, the photoacoustic detector unit 700 can for example at least partly be similar to the photoacoustic detector unit 600 in FIG. 6 and comprise identical components.

The photoacoustic detector unit 700 can comprise a photoacoustic transducer 6 in the form of a membrane 70. In contrast to FIG. 6, the membrane 70 can be fabricated from a doped semiconductor material. On account of the doping of the semiconductor material, the membrane 70 can be designed to absorb optical radiation and to convert it into at least one from a pressure signal or a heat signal. In one example, the membrane 70 can be fabricated from silicon and be doped with at least one from boron, phosphorus, aluminum, indium, arsenic, antimony.

In a further contrast to FIG. 6, the photoacoustic transducer 6 can furthermore comprise an optically transparent cover 76, which can be connected to the membrane 70 and can form with the latter an (in particular hermetically sealed) cavity 10. The cover 76 can be fabricated from silicon, for example. If the cover 76 and the membrane 70 are fabricated from silicon, they can be secured to one another by way of a eutectic silicon-silicon bond connection, for example. As evident from the method in FIGS. 12A-E, it is possible to carry out eutectic bonding using an intermediate layer at the wafer level. The intermediate layer can be fabricated from gold, for example.

In yet another contrast to FIG. 6, the photoacoustic transducer 6 can optionally comprise an optical filter layer 78, which can be arranged for example on the top side of the cover 76. The optical filter layer 78 can be transmissive to electromagnetic radiation in a predetermined wavelength range. The wavelength range can comprise, in particular, an absorption band of a gas to be detected.

A reference gas can optionally be enclosed in the hermetically sealed cavity 10. In this case, the photoacoustic detector unit 700 in FIG. 7 can be used for example in the photoacoustic sensor 100 in FIG. 1.

Figure 8:
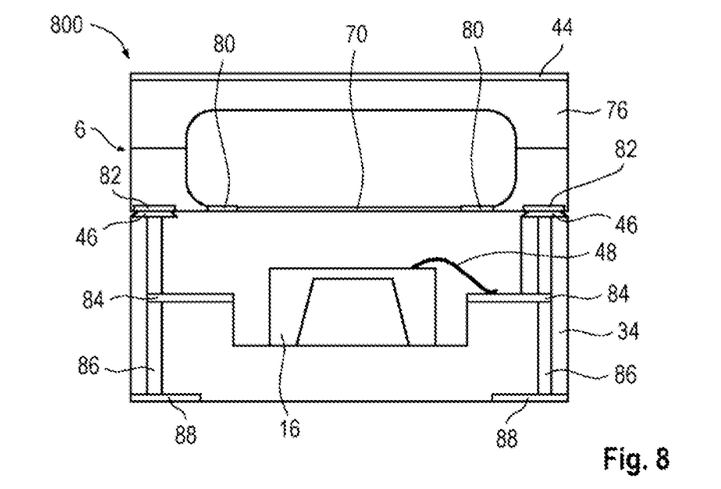
FIG. 8 schematically illustrates a cross-sectional side view of a photoacoustic detector unit 800 in accordance with the disclosure.

The photoacoustic detector unit 800 in FIG. 8 can at least partly be similar to the photoacoustic detector unit 700 in FIG. 7 and comprise identical components, such that explanations concerning FIG. 7 can also apply to the photoacoustic detector unit 800.

In contrast to FIG. 7, the photoacoustic detector unit 800 can additionally comprise one or more piezo-elements 80 integrated into the membrane 70. In this case, the piezo-elements 80 can be arranged for example at the edge region of the membrane 70 or at a suspension of the inner region of the membrane 70. The piezo-elements 80 can be designed to provide an electrical signal designed as a reference signal for a measurement signal provided by the pressure pick-up 16. By way of example, undesired acoustic influences that can occur during operation of the photoacoustic detector unit 800 can be averaged out on the basis of a comparison of the measurement signal with the reference signal. The membrane 70 can have electrical contact pads 82 on its underside, by way of which reference signals generated by the piezo-elements 80 can be provided.

In a further contrast to FIG. 7, the housing 34 can be embodied in a different way. The housing 34 in FIG. 8 can be produced from a ceramic material, for example. In the cross-sectional side view in FIG. 8, the housing 34 can have a stepped shape. The pressure pick-up 16 can be arranged on the bottom surface of the housing 34. Electrical contact pads 84 can be arranged on the top sides of the steps, and can be electrically connected to via connections 86 extending perpendicularly through the housing 34. Further contact pads 88 can be arranged on the underside of the housing 34. Reference signals detected by the piezo-elements 80 can be forwarded to one or more of the contact pads 88 by way of the contact pads 82 and by way of the via connections 86. In a similar way, measurement signals of the pressure pick-up 16 can be forwarded to one or more of the contact pads 88 by way of the contact pads 84 and the via connections 86.

Figure 9:
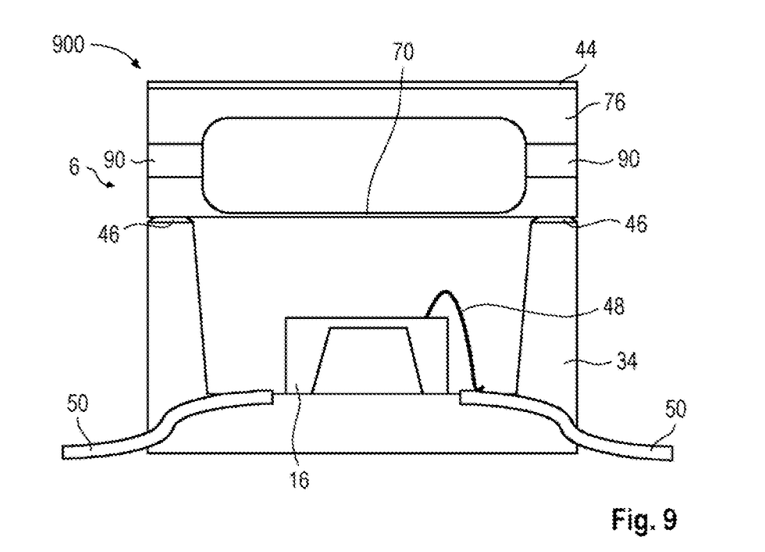
FIG. 9 schematically illustrates a cross-sectional side view of a photoacoustic detector unit 900 in accordance with the disclosure.

The photoacoustic detector unit 900 in FIG. 9 can be at least partly similar to the photoacoustic detector unit 700 in FIG. 7. In contrast to FIG. 7, the photoacoustic transducer 6 can comprise an additional intermediate layer 90, which can be arranged between the membrane 70 and the cover 76. The intermediate layer 90 can be designed to simplify connection of the membrane 70 to the cover 76 in terms of process engineering. By way of example, the membrane 70 can be fabricated from doped silicon and the cover 76 can be fabricated from silicon. In such a case, the intermediate layer 90 can be fabricated from a glass material, in particular a borosilicate. As a result, the membrane 70 and the cover 76 can be connected to the intermediate layer 90 in each case by anodic bonding. Furthermore, a use of the intermediate layer 90 makes it possible to adapt or increase the structural height of the photoacoustic transducer 6 in the y-direction in a simple manner.

Figure 10:
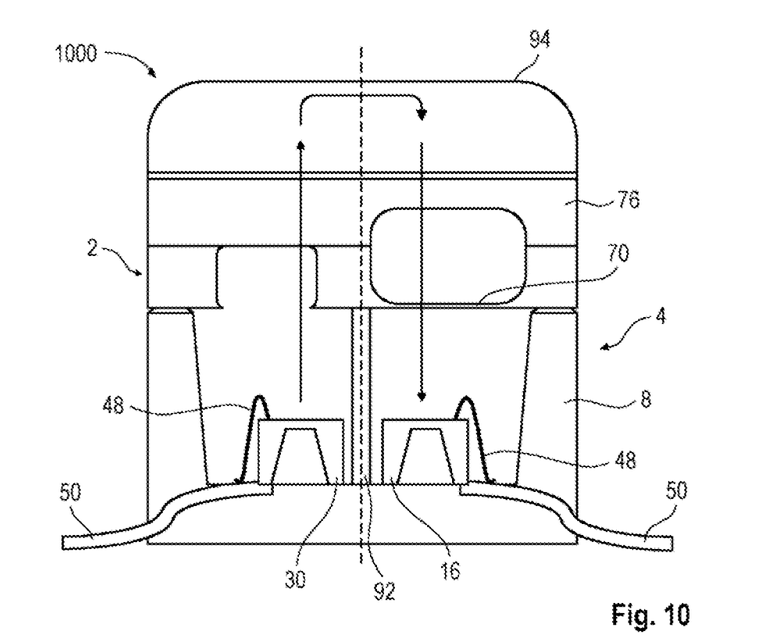
FIG. 10 schematically illustrates a cross-sectional side view of a photoacoustic sensor 1000 in accordance with the disclosure.

The photoacoustic sensor 1000 in FIG. 10 can be similar to one of the photoacoustic sensors 100 and 200 in FIGS. 1 and 2. In particular, the construction shown in FIG. 10 can be used for a realization of the photoacoustic sensors in FIGS. 1 and 2.

The photoacoustic sensor 1000 in FIG. 10 can comprise a photoacoustic emitter unit 2 and a photoacoustic detector unit 4. A spatial separation of the units 2 and 4 is indicated qualitatively in FIG. 10 by a perpendicularly extending dashed line. In the example in FIG. 10, the photoacoustic detector unit 4 can for example be similar to the photoacoustic detector unit 700 in FIG. 7, such that in this regard reference can be made to explanations concerning FIG. 7.

The photoacoustic sensor 1000 can comprise a housing 8, which can be separated into a left and right part by a separating structure 92. In this case, the right part of the housing 8 can correspond to the housing 34 in FIG. 7. An optical emitter 30 can be arranged on the left part of the housing 8. Depending on the implementation of the photoacoustic detector unit 4, the optical emitter 30 can be a broadband emitter with or without a downstream optical bandpass filter. The photoacoustic sensor 1000 can furthermore comprise a cover 94 having an optically reflective inner surface, the cover being arranged above the units 2 and 4.

During operation of the photoacoustic sensor 1000, the emitter 30 can emit optical radiation that can propagate along an optical path represented by three arrows in FIG. 10. The emitter 30 can emit optical radiation in the direction of the cover 94. The emitted radiation can be reflected at the inner surface of the cover 94. In order to be able to provide the reflection course illustrated qualitatively in FIG. 10, the inner surface of the cover 94 can be shaped in a suitable manner. The optical radiation reflected from the inner surface of the cover 94 can impinge on the photoacoustic detector unit 4.

FIGS. 12A-E illustrate a flow diagram of a method in accordance with the disclosure. By way of example, one or more photoacoustic transducers for a photoacoustic detector unit in accordance with the disclosure can be produced with the aid of the method.

Figure 11:
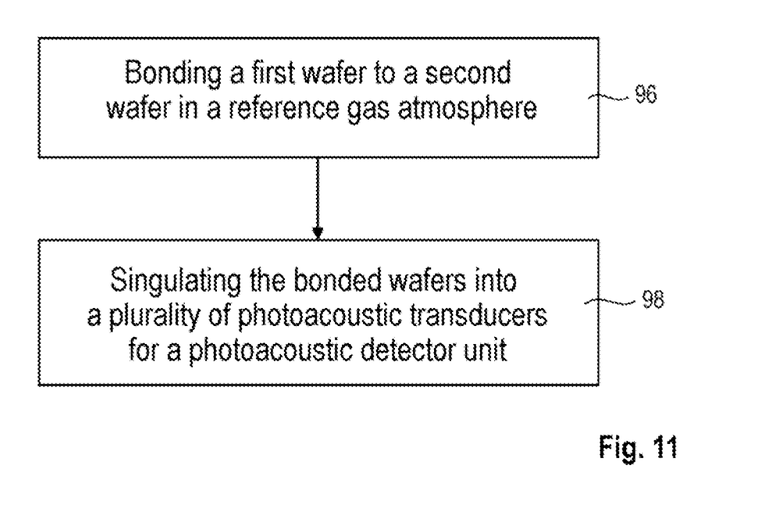
FIG. 11 illustrates a flow diagram of a method in accordance with the disclosure.

At 96 a first wafer composed of a first material is bonded to a second wafer composed of a second material in a reference gas atmosphere. In this case, a plurality of hermetically sealed cavities are formed, which enclose the reference gas of the reference gas atmosphere. At 98 the bonded wafer is singulated into a plurality of photoacoustic transducers for a photoacoustic detector unit. In this case, each of the photoacoustic transducers comprises one of the hermetically sealed cavities.

Figure 12A:
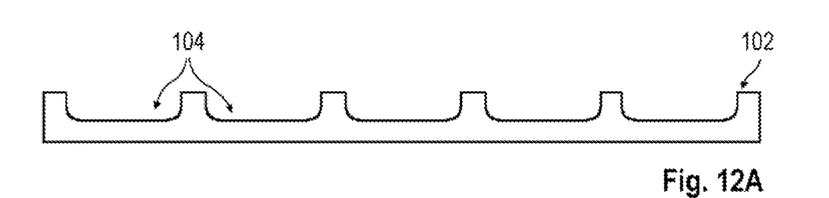
FIGS. 12A to 12E schematically illustrate a cross-sectional side view of a method for producing a photoacoustic transducer 1200 for a photoacoustic detector unit in accordance with the disclosure.

The method in FIGS. 12A-E can be regarded as a more detailed implementation of the method in FIG. 11. In FIG. 12A, a first wafer 102 composed of a first material can be provided. The first wafer 102 can have a multiplicity of depressions 104. In this case, the number of depressions 104 can correspond, in particular, to a number of photoacoustic transducers to be produced by the method in FIGS. 12A-E. In the cross-sectional side view in FIG. 12A, the depressions 104 can have a rounded shape. In further examples, the shape of the depressions 104 can be chosen differently, for example square, rectangular, polygonal, etc. The first wafer 102 can be fabricated from a glass material or a doped semiconductor material, for example.

Figure 12B:
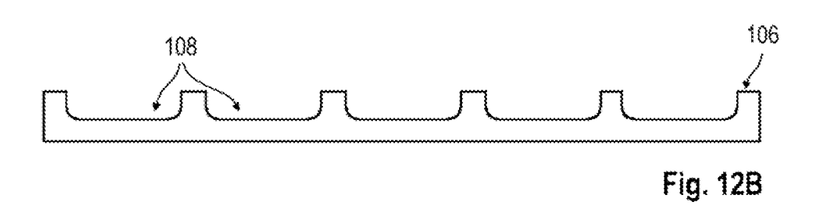

In FIG. 12B, a second wafer 106 composed of a second material can be provided. The second wafer 106 can have a multiplicity of depressions 108. The number of depressions 108 can correspond in particular to the number of depressions 104 of the first wafer 102. In the example in FIG. 12B, the depressions 108 can have a rounded shape. In further examples, the shape of the depressions 108 can be chosen differently, for example square, rectangular, polygonal, etc. The second wafer 106 can be fabricated from a semiconductor material, for example.

Figure 12C:
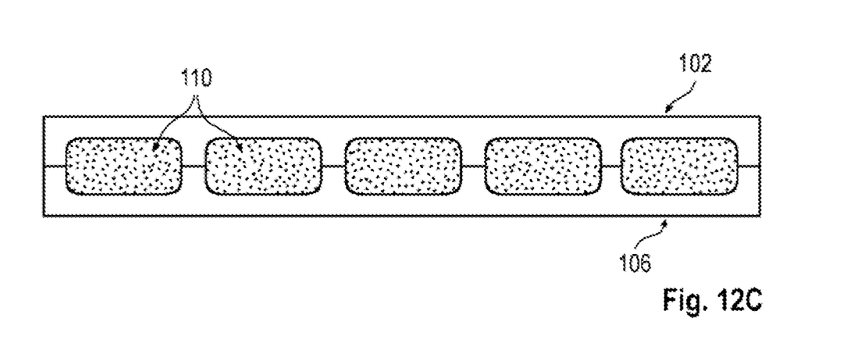

In FIG. 12C, the first wafer 102 can be bonded to the second wafer 106 in a reference gas atmosphere. For the bonding process, the first wafer 102 and the second wafer 106 can be arranged in a bonding chamber (not illustrated) designed to provide the reference gas atmosphere. During the bonding of the wafers 102 and 106, a plurality of hermetically sealed cavities 110 can be formed, which enclose the reference gas of the reference gas atmosphere.

The bonding process employed in FIG. 12C can be dependent in particular on the materials of the wafers 102 and 106. In a first example, the material of the first wafer 102 can comprise a glass material (e.g. a borosilicate) and the material of the second wafer 106 can comprise a semiconductor material (e.g. silicon). In this case, the bonding process can comprise anodic bonding. In a second example, the material of the first wafer 102 can comprise a doped semiconductor material (e.g. doped silicon) and the material of the second wafer 106 can comprise a semiconductor material (e.g. silicon). In this case, the bonding process can comprise eutectic bonding using an intermediate layer. The intermediate layer can be fabricated from gold, for example.

Figure 12D:
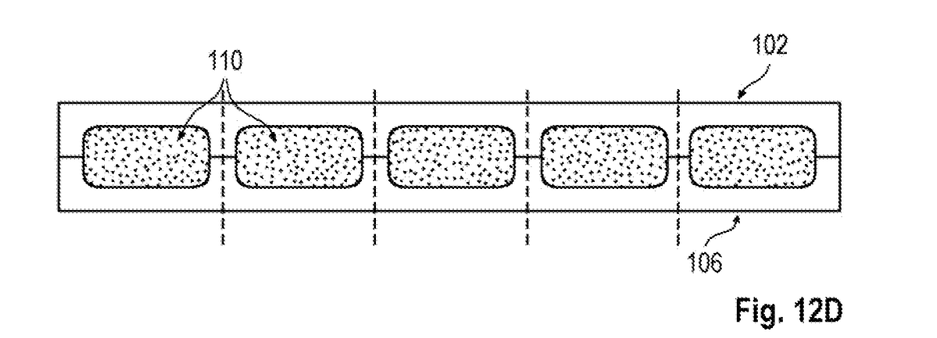

In FIG. 12D, the arrangement from FIG. 12C can be singulated into a plurality of arrangements along perpendicular dashed lines. The singulating process can include for example an etching process, a plasma dicing process, a mechanical ultrasonic dicing process, a laser dicing process, or a combination thereof.

Figure 12E:
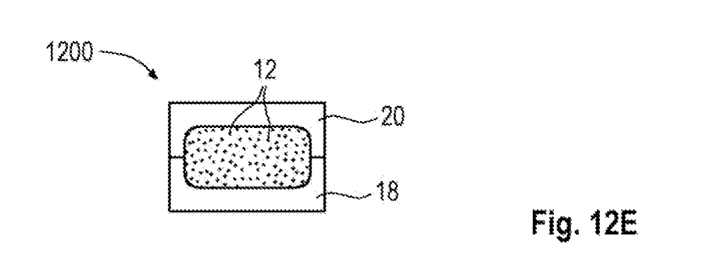

FIG. 12E shows one of the photoacoustic transducers 1200 obtained as a result of the singulation, which photoacoustic transducer can comprise an optically transparent window 18 and a membrane 20. In this case, the membrane 20 can be fabricated from the material of the first wafer 102 and the optically transparent window 18 can be fabricated from the material of the second wafer 106.

The method in FIGS. 12A-E can comprise further steps, which are not explicitly illustrated and discussed for the sake of simplicity. The further steps can be carried out here in particular at the wafer level. By way of example, the method can be extended by a step in which an antireflection coating can be applied on the second wafer 106, such that the photoacoustic transducers 1200 produced can each have an antireflection coating on the optically transparent window 18.

Examples

Photoacoustic detector units, photoacoustic sensors and associated production methods are explained below on the basis of examples.

Example 1 is a photoacoustic detector unit, comprising: a housing having an opening; a photoacoustic transducer designed to convert optical radiation into at least one from a pressure signal or a heat signal, wherein the photoacoustic transducer covers the opening of the housing, such that the photoacoustic transducer and the housing form an acoustically tight cavity; and a pressure pick-up arranged in the acoustically tight cavity.

Example 2 is a photoacoustic detector unit according to example 1, wherein the photoacoustic transducer is designed to convert at least one from infrared radiation or ultraviolet radiation into at least one from a pressure signal or a heat signal.

Example 3 is a photoacoustic detector unit according to example 1 or 2, wherein the photoacoustic transducer comprises: a cell having a hermetically sealed cavity; and a reference gas enclosed in the hermetically sealed cavity, wherein the reference gas is designed to absorb the optical radiation.

Example 4 is a photoacoustic detector unit according to example 3, wherein the cell comprises: an optically transparent window on a first side of the cell; and a membrane on a second side of the cell, the second side being situated opposite the first side.

Example 5 is a photoacoustic detector unit according to example 4, wherein the optically transparent window is fabricated from silicon.

Example 6 is a photoacoustic detector unit according to example 4 or 5, wherein the membrane is fabricated from a glass material.

Example 7 is a photoacoustic detector unit according to any of examples 4 to 6, wherein the membrane is fabricated from doped silicon.

Example 8 is a photoacoustic detector unit according to any of examples 4 to 7, wherein the optically transparent window and the membrane form the hermetically sealed cavity.

Example 9 is a photoacoustic detector unit according to any of examples 4 to 8, wherein the optically transparent window and the membrane are wafer-bonded.

Example 10 is a photoacoustic detector unit according to any of examples 4 to 9, furthermore comprising: an antireflection coating arranged on the optically transparent window.

Example 11 is a photoacoustic detector unit according to any of examples 4 to 10, furthermore comprising: a metal layer arranged on the membrane.

Example 12 is a photoacoustic detector unit according to any of the preceding examples, furthermore comprising: a protective gas enclosed in the acoustically tight cavity.

Example 13 is a photoacoustic detector unit according to any of the preceding examples, wherein the housing is fabricated from a mold compound.

Example 14 is a photoacoustic detector unit according to example 1, wherein the photoacoustic transducer comprises: a membrane designed to absorb the optical radiation.

Example 15 is a photoacoustic detector unit according to example 14, wherein the membrane is fabricated from at least one from glass material or doped silicon.

Example 16 is a photoacoustic detector unit according to example 14 or 15, furthermore comprising: a piezo-element integrated into the membrane and designed to provide an electrical signal designed as a reference signal for a measurement signal provided by the pressure pick-up.

Example 17 is a photoacoustic detector unit according to any of examples 14 to 16, furthermore comprising: an optical filter layer, which is transmissive to electromagnetic radiation of a predetermined wavelength, wherein the optical filter layer is applied on at least one from the membrane or a cover arranged above the membrane.

Example 18 is a photoacoustic sensor, comprising: an optical emitter; and a photoacoustic detector unit according to any of the preceding examples.

Example 19 is a photoacoustic sensor according to example 18, wherein the optical emitter comprises an optical broadband emitter.

Example 20 is a photoacoustic sensor according to example 19, furthermore comprising: an optical bandpass filter disposed downstream of the optical broadband emitter, the optical bandpass filter being transmissive to electromagnetic radiation of a predetermined wavelength.

Example 21 is a method, comprising: bonding a first wafer composed of a first material to a second wafer composed of a second material in a reference gas atmosphere, wherein a plurality of hermetically sealed cavities are formed, which enclose the reference gas of the reference gas atmosphere; and singulating the bonded wafers into a plurality of photoacoustic transducers for a photoacoustic detector unit, wherein each of the photoacoustic transducers comprises one of the hermetically sealed cavities.

Example 22 is a method according to example 21, wherein: the first material comprises a glass material, the second material comprises a semiconductor material, and the bonding comprises anodic bonding.

Example 23 is a method according to example 21, wherein: the first material comprises a doped semiconductor material, the second material comprises a semiconductor material, and the bonding comprises eutectic bonding using an intermediate layer.

Although specific implementations have been illustrated and described herein, it is obvious to the person of average skill in the art that a multiplicity of alternative and/or equivalent implementations can replace the specific implementations shown and described, without departing from the scope of the present disclosure. This application is intended to cover all adaptations or variations of the specific implementations discussed herein. Therefore, the intention is for this disclosure to be restricted only by the claims and the equivalents thereof.

What is claimed is:

1. A method, comprising:
    bonding a first wafer, composed of a first material, to a second wafer, composed of a second material, in a reference gas atmosphere to form bonded wafers,
        wherein a plurality of hermetically sealed cavities are formed,
        wherein the plurality of hermetically sealed cavities enclose a reference gas of the reference gas atmosphere; and
    singulating the bonded first and second wafers into a plurality of photoacoustic transducers for a photo acoustic detector unit,
        wherein each photoacoustic transducer, of the plurality of photoacoustic transducers, comprises a respective hermetically sealed cavity, of the plurality of hermetically sealed cavities, and
        wherein each photoacoustic transducer, of the plurality of photoacoustic transducers, is configured to cover an opening of a housing of a photoacoustic detector unit to form an acoustically tight cavity.

2. The method as claimed in claim 1, wherein the first material comprises a glass material and the second material comprises a semiconductor material.

3. The method of claim 2, wherein bonding the first wafer to the second wafer comprises:
    anodic bonding the first wafer to the second wafer.

4. The method of claim 3, wherein bonding the first wafer to the second wafer comprises:
    eutectic bonding, using an intermediate layer, the first wafer to the second wafer.

5. The method as claimed in claim 1, wherein the first material comprises a doped semiconductor material and the second material comprises a semiconductor material.

6. The method as claimed in claim 1, wherein the reference gas is designed to absorb optical radiation.

7. The method as claimed in claim 6, wherein the optical radiation comprises one or more of ultraviolet radiation, infrared radiation, or radiation having a wavelength of within a range of 780 nm to 5 μm.

8. The method as claimed in claim 1, wherein the reference gas comprises carbon dioxide, nitrogen oxide, methane, or ammonia.

9. The method as claimed in claim 1, further comprising:
    at least partially absorbing, by a hermetically sealed cavity, of the plurality of hermetically sealed cavities, of a photoacoustic transducer, of the plurality of photoacoustic transducers, an optical pulse.

10. The method as claimed in claim 1, wherein a photoacoustic transducer, of the plurality of photoacoustic transducers, is included in a photoacoustic sensor, the method further comprising:
    converting optical radiation into one or more pressure signals,
        wherein the optical radiation is emitted by a photoacoustic emitter unit of the photoacoustic sensor.

11. The method as claimed in claim 10, wherein the optical radiation comprises one or more optical pulses, and wherein converting the optical radiation into the one or more pressure signals comprises:
    at least partially absorbing the one or more optical pulses,
        wherein at least partially absorbing the one or more optical pulses causes a localized increase in a pressure of the reference gas, and
        wherein the optical radiation is converted into the one or more pressure signals based on the localized increase in the pressure of the reference gas.

12. A method, comprising:
    forming a plurality of hermetically sealed cavities based on bonding a first wafer, composed of a first material, to a second wafer, composed of a second material, in a reference gas atmosphere,
        wherein bonding the first wafer to the second wafer forms bonded wafers, and
        wherein the plurality of hermetically sealed cavities enclose a reference gas of the reference gas atmosphere; and
    forming a plurality of photoacoustic transducers for a photoacoustic detector unit based on singulating the bonded wafers,
        wherein each photoacoustic transducer, of the plurality of photoacoustic transducers, comprises a respective hermetically sealed cavity, of the plurality of hermetically sealed cavities, and
        wherein each photoacoustic transducer, of the plurality of photoacoustic transducers, is configured to cover an opening of a housing of a photoacoustic detector unit to form an acoustically tight cavity.

13. The method as claimed in claim 12, wherein the first material comprises a glass material and the second material comprises a semiconductor material, and wherein forming the plurality of hermetically sealed cavities comprises:
forming the plurality of hermetically sealed cavities based on anodic bonding the first wafer to the second wafer.

14. The method as claimed in claim 12, wherein the first material comprises a doped semiconductor material and the second material comprises a semiconductor material, and wherein forming the plurality of hermetically sealed cavities comprises:
forming the plurality of hermetically sealed cavities based on eutectic bonding the first wafer to the second wafer using an intermediate layer.

15. The method as claimed in claim 12, wherein the reference gas is designed to absorb optical radiation.

16. The method as claimed in claim 15, wherein the optical radiation comprises one or more of ultraviolet radiation, infrared radiation, or radiation having a wavelength of within a range of 780 nm to 5 μm.

17. The method as claimed in claim 12, wherein the reference gas comprises carbon dioxide, nitrogen oxide, methane, or ammonia.

18. The method as claimed in claim 12, further comprising:
at least partially absorbing, by a hermetically sealed cavity of a photoacoustic transducer, of the plurality of photoacoustic transducers, an optical pulse.

19. The method as claimed in claim 12, wherein a photoacoustic transducer, of the plurality of photoacoustic transducers, is included in a photoacoustic sensor, the method further comprising:
converting optical radiation into one or more pressure signals,
wherein the optical radiation is emitted by a photoacoustic emitter unit of the photo acoustic sensor.

20. The method as claimed in claim 19, wherein the optical radiation comprises one or more optical pulses, and wherein converting the optical radiation into the one or more pressure signals comprises:
at least partially absorbing the one or more optical pulses,
wherein at least partially absorbing the one or more optical pulses causes a localized increase in a pressure of the reference gas, and
wherein the optical radiation is converted into the one or more pressure signals based on the localized increase in the pressure of the reference gas.

* * * * *